(12) United States Patent
Jackson

(10) Patent No.: US 6,666,888 B1
(45) Date of Patent: Dec. 23, 2003

(54) THREADED FUSION CAGE WITH ENHANCED ANTERIOR SUPPORT

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 140 days.

(21) Appl. No.: 09/644,722

(22) Filed: Aug. 23, 2000

(51) Int. Cl.$^7$ .................................................. A61F 2/44
(52) U.S. Cl. .................................................. 623/17.11
(58) Field of Search .................. 623/17.11, 17.16; A61F 2/44

(56) References Cited

U.S. PATENT DOCUMENTS

| | | |
|---|---|---|
| 5,458,638 A | 10/1995 | Kuslich et al. |
| 5,489,308 A | 2/1996 | Kuslich et al. |
| 5,609,636 A | 3/1997 | Kohrs et al. |
| 5,658,337 A | 8/1997 | Kohrs et al. |
| 5,665,122 A | 9/1997 | Kambin |
| 5,669,909 A | 9/1997 | Zdeblick et al. |
| 5,782,919 A | 7/1998 | Zdeblick et al. |
| 5,865,847 A | 2/1999 | Kohrs et al. |
| 5,968,098 A | 10/1999 | Winslow |
| 6,053,916 A * | 4/2000 | Moore ................ 623/18.11 |
| 6,224,631 B1 * | 5/2001 | Kohrs ................ 623/17.11 |
| 6,436,139 B1 * | 8/2002 | Shapiro et al. ........ 623/17.11 |

* cited by examiner

*Primary Examiner*—Corrine McDermott
*Assistant Examiner*—Brian E Pellegrino
(74) *Attorney, Agent, or Firm*—John C. McMahon

(57) ABSTRACT

A threaded fusion cage for implantation between a pair of vertebrae. The cage has a discontinuous thread helically wound thereabout. The thread has a constant depth in posterior and middle portions of the cage but is feathered in an anterior portion of the cage so that the minor radius approaches or equals the major radius of the thread. This provides greater support to the relatively stronger and harder bone found at the anterior end of the vertebrae.

9 Claims, 2 Drawing Sheets

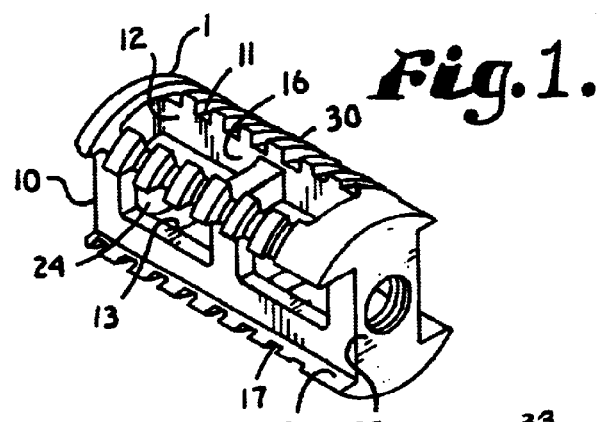
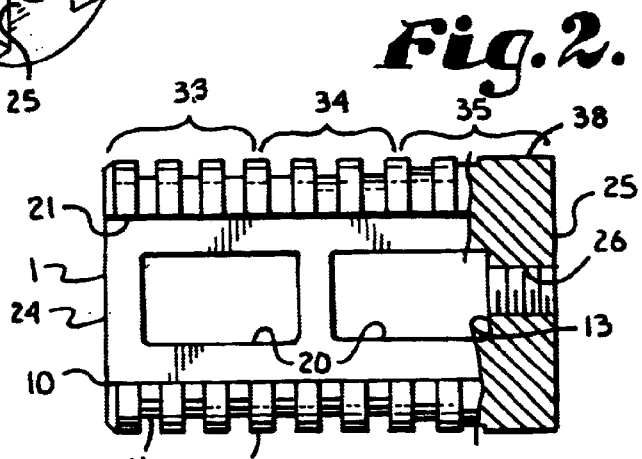
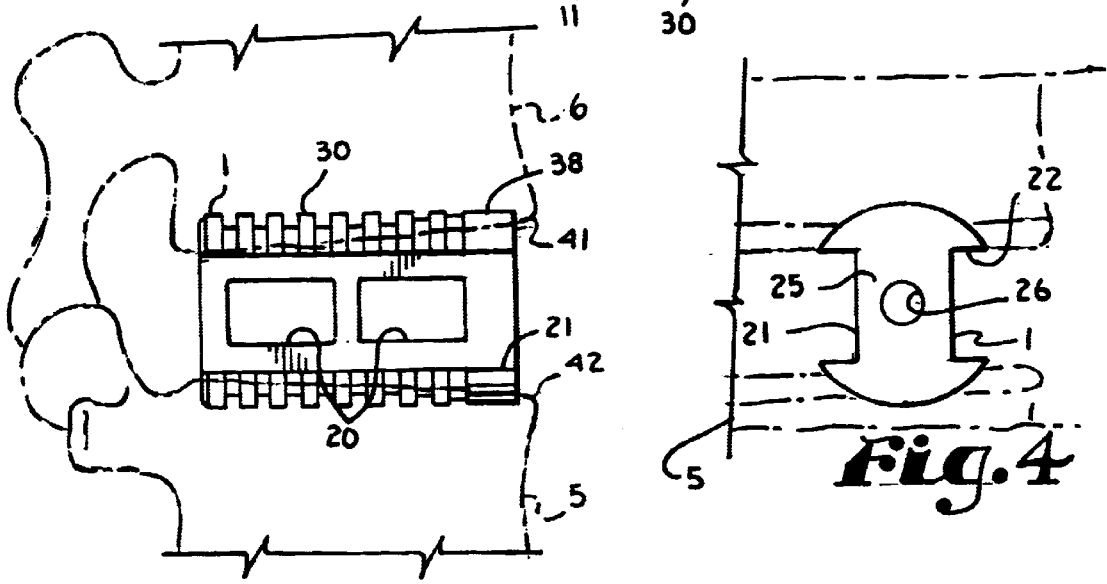

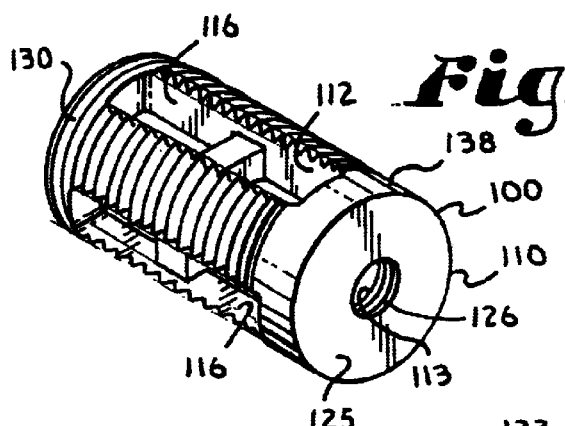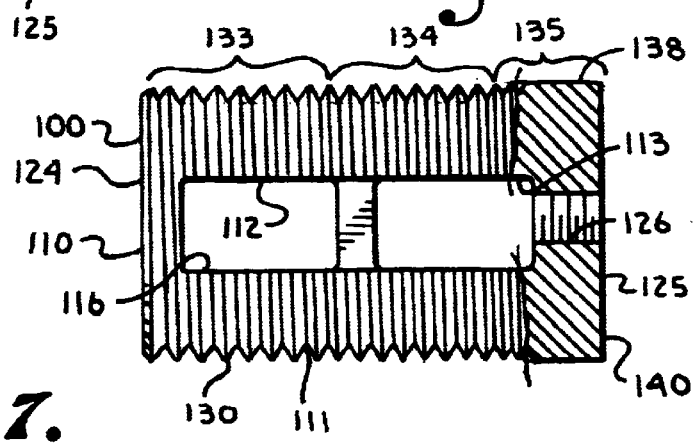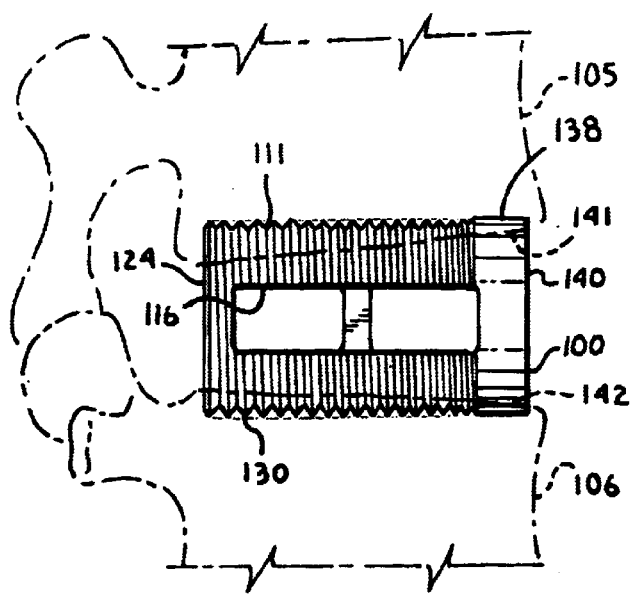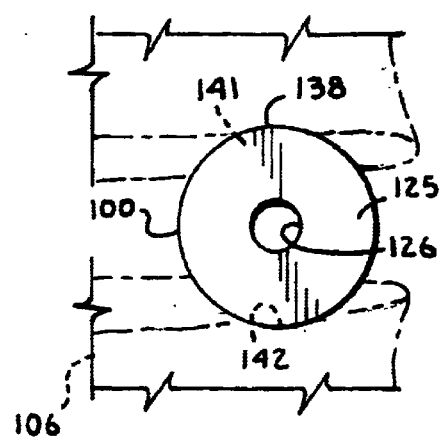

THREADED FUSION CAGE WITH ENHANCED ANTERIOR SUPPORT

BACKGROUND OF THE INVENTION

The present application is directed to a fusion cage for use as a spinal implant between a pair of vertebrae in order to provide support to and subsequently promote the fusing together of the vertebrae and, in particular, a threaded fusion cage having a thread that is feathered near an anterior end of the fusion cage, such that a minor diameter of the thread approaches a major diameter of the thread near the anterior end.

Fusion cages are commonly implanted between a pair of vertebrae of the spine in order to provide support to the vertebrae and to eventually promote fusion between the vertebrae. Fusion cages are generally of two types which are rectangular in cross-section or circular in cross-section. The present application is directed to the latter type which are overall generally cylindrical in shape and threaded so as to provide a better grip for the cage upon implantation. The threaded cages are normally inserted between vertebrae where the disc between the vertebrae has been removed and a partial bore has been provided by drilling or the like. Normally, the fusion cages will have windows extending between the top and bottom thereof to allow bone to grow through and fuse together between the vertebrae. Also the interior of the fusion cage is often packed with bone or other matrix that encourages the growth of bone into the cage and between the two vertebrae and, therefore, a subsequent fusing therebetween.

The facing surfaces of the vertebrae between which the cages are inserted are mostly of a relatively soft spongy bone. Because of this, the cages are subject to subsiding into the bone either very soon after surgery or at a later date. Such subsidence is undesirable.

While the majority of the bone adjacent the facing surfaces of the vertebrae is spongy and somewhat soft, a comparatively narrow band of bone at the anterior of each vertebrae is comparatively harder bone. It is, therefore, desirable to take advantage of this harder bony region by improving the contact of the fusion cages, as much as possible, in this region and reducing structure into which the bone can subside.

SUMMARY OF THE INVENTION

A fusion cage has a cylindrical or partially cylindrical shape with a pair of semi-circular surfaces on opposite sides thereof that are sized and shaped to engage facing surfaces of a pair of vertebrae that are to be supported and fused by the fusion cage. The fusion cage surfaces include a thread thereon that may be continuous about the fusion cage, but is normally only on the surfaces that engage the vertebrae during actual use and, in such cases, a complementary thread may be provided by an insertion tool to allow the device to be threadedly advanced into a bore located between the two adjacent vertebrae. For example, see U.S. Pat. No. 5,865,847 of Kohrs et al. which is incorporated herein by reference.

The thread has a major diameter and a minor diameter. Over most of the length of the cage and especially near the posterior end of the cage, the minor diameter is substantially less than the major diameter thereby forming a series of peaks and valleys constituting the threadform. The major diameter of the thread stays generally constant along the entire length of the thread. The thread depth remains generally constant near the posterior end and middle of the cage, but is reduced near the anterior end of the cage.

In particular, located near the anterior end of the cage and sized and positioned to engage an anterior surface of comparatively harder bone near the anterior of the vertebrae is a modified thread. In the modified thread the minor diameter approaches and preferably equals the major diameter at the front or anterior end of the cage to effectively reduce the thread depth in this region. Preferably, the minor diameter over a short distance approaches the major diameter evenly or progressively, as the threadform winds discontinuously, but in a helical form or pattern about the cage. Also preferably the increased minor diameter occurs over approximately at least the front ¼ inch of the thread, while the major diameter remains constant. Further, the minor diameter is preferably approximately equivalent to or the same height as the major diameter between the final two passes of the threadform near the anterior end of the cage so as to present a generally smooth cylindrical or semi-cylindrical surface in this region.

OBJECTS AND ADVANTAGES OF THE INVENTION

Therefore, the objects of the present invention are: to provide a fusion cage for implantation between a pair of vertebrae, so as to provide support and fusion between the vertebrae, and that resist subsidence into the vertebrae by providing as much support as possible near an anterior end of the fusion cage whereat the fusion cage engages a harder bony region of the vertebrae; to provide such a cage that is generally cylindrical in shape and threaded; to provide such a cage having a thread with a major diameter and a minor diameter that is helical in form, but is not continuous, that is wound about the cage; to provide such a cage wherein the thread is feathered near the anterior end of the cage by increasing the minor diameter of the thread, while maintaining the major diameter constant, until the minor diameter approaches or equals the major diameter of the thread, so as to reduce thread depth at the anterior end of the cage; to provide such a cage having a generally smooth cylindrical surface at the anterior end thereof that is at least the equivalent of several thread turns in width; and to provide such a cage wherein the minor diameter of the thread is allowed to increase evenly and progressively over approximately ¼ of an inch length of the cage until it approaches or is equal to the major diameter; to provide such a cage which is comparatively easy to construct, easy to use and especially well adapted for the intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a fusion cage in accordance with the present invention.

FIG. 2 is a side elevational view of the fusion cage with portions broken away to show detail thereof.

FIG. 3 is a side elevational view of the fusion cage mounted between a pair of vertebrae that are shown in phantom.

FIG. 4 is a front elevational view of the fusion cage positioned between a pair of vertebrae that are shown in phantom.

FIG. 5 is a perspective view of a modified fusion cage in accordance with the present invention.

FIG. 6 is a side elevational view of the modified fusion cage with portions broken away to show detail thereof.

FIG. 7 is a side elevational view of the fusion cage mounted between a pair of vertebrae that are shown in phantom.

FIG. 8 is a front elevational view of the fusion cage positioned between a pair of vertebrae that are shown in phantom.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference number 1 generally designates a fusion cage in accordance with the present invention. The fusion cage 1 is normally used side by side in pairs located between a pair of adjacent vertebrae 5 and 6, as seen in FIG. 3.

The cage 1 has an overall generally cylindrical shaped body 10 with portions removed, as described below, and with an outer surface 11 located on and defined by an exterior of a wall 12. An inner open chamber 13 is also defined by an interior of the wall 12.

In the illustrated embodiment the wall 12 includes upper and lower fenestrations or windows 16 and 17, as well as side windows 20.

The sides of the cage body 10 are truncated and channeled to produce channels 21 and 22 so as to reduce weight and size and to allow for mating with a tool (not shown) used in a well known process for inserting the cage 1 between the vertebrae 5 and 6.

The cage 1 also has a rear wall 24 and a front wall 25. The front wall 25 includes an aperture or threaded bore 26 that allows for the packing of the chamber 13 during the installation process. The packed bone and other growth promoting matrix enhance the fusion of the bone of the vertebrae 5 and 6 through the windows 16 and 17.

Formed on the cage surface 11 is a thread 30. The thread 30 is discontinuously wound about the surface 11 in a helical pattern and mates with similar thread on a tool (not shown) for purposes of insertion after which the tool is removed. It is noted that in accordance with the invention, the thread 30 can have varying degrees of discontinuity depending upon the particular type of cylindrical threaded cage used. That is, some such cages have outer surfaces that are continuous or almost continuous, while others have more windows and other openings. The thread 30 of this embodiment has an outer radius and an inner radius and is somewhat step-like or square in form. The thread outer radius remains generally constant throughout the length of both the thread 30 and the cage 1.

The thread inner radius remains constant over a posterior 33 portion and a middle portion 34 of the cage 1, but varies near a front or anterior portion 35 so as to vary the thread depth in the cage anterior portion 35 as compared to the rest of the cage 1.

In particular, the minor radius approaches or equals the major radius over at least part of the anterior portion 34. Preferably, the minor radius or the bottom of the thread increases radially outward evenly or progressively over two or three turns of the thread 30 at or near the anterior end of the cage 1. That is, preferably, the thread depth is feathered over the last few turns to reduce the depth and to provide greater support to bone adjacent thereto and reduce the likelihood of subsidence of the cage 1 into the bone. As used herein, the term turn means a single, but discontinuous, pass of the thread 30 in a 360° arc around the cage 1. Thus, the thread inner diameter or radius keeps increasing in the anterior portion 35 as the thread 30 approaches the front of the cage 1. Also, preferably, the inner diameter equals the outer diameter over the last two turns of the thread 1, so as to produce a generally smooth cylindrical surface 38. The thread 30 minor radius preferably increases over about the forward or anterior one fourth inch of the cage 1.

In use the cage 1 is inserted, as a side by side generally parallel pair, between the vertebrae 5 and 6 after removal of a pad therebetween and boring between the vertebrae 5 and 6 to create an opening approximately the shape of the cage outer surface 11. Each vertebrae 5 and 6 has an anterior relatively hard boney region 41 and 42 respectively. The cage 1 is positioned such that the thread anterior portion 35, where the thread depth is not as great because the minor radius is increased in comparison to the rest of the thread, is located in abutting relationship to the regions 41 and 42. The cylindrical surface 38 is especially located to support the regions 41 and 42 on either side of the cage 1.

Shown in FIGS. 5 through 8 is a second embodiment of a fusion cage 100 in accordance with the present invention. The cage 100 is similar in many aspects to the cage 1, so that the same features will not be reiterated in detail, but rather reference is made to the first embodiment for greater detail.

The cage 100 is shown positioned between two vertebrae 105 and 106 in FIGS. 6 and 7. Normally, a pair of the cages 100 is used in parallel spaced relationship or with a slight toe in or toe out with respect to one another.

The cage 100 has a body 110 with a windowed, but otherwise generally cylindrically shaped outer surface 111, defined by a wall 112. The wall also defines an inner chamber 113. Four evenly spaced windows 116 extend between the outer surface 111 and chamber 113. The cage has a rear wall 124 and a front wall 125 with a bore 126 therein.

A thread 130 is wrapped about the length of the cage 1. The thread 130 is laid in a helical pattern, but is discontinuous at the windows 116.

The thread 130 of the present embodiment is V-shaped as opposed to the step or square threadform of the previous embodiment.

The thread 130 is tapered or feathered near the anterior end 140 of the cage 1. In particular, the thread 130 has a rear portion 133, a middle portion 134 and a front or anterior portion 135. In the rear portion 133 and the middle portion 134 the thread 130 has a generally constant or uniform thread depth between the major and minor radii of the thread 130. Whereas, the thread depth of the thread 130 in the anterior portion 135 approaches or equals zero or no depth. Preferably the minor radius of the thread 130 increases progressively in the front portion 135 for several turns until the minor radius equals the major radius very near the anterior end 140 of the cage 1 and preferably at least over the last turn of the thread 130, so as to provide a generally smooth cylindrical surface 138 in this region to resist subsidence into the vertebrae 105 and 106. The surface 138 is especially sized, shaped and positioned during use to engage or abut the harder boney regions 141 and 142 of the vertebrae 105 and 106.

It is to be understood that while certain forms of the present invention have been illustrated and described herein, it is not to be limited to the specific forms or arrangement of parts described and shown.

What is claimed and desired to be secured by letters patent is as follows:

1. A spinal fusion cage for implantation between a pair of vertebra; said cage comprising:
   a) an elongate body having semi-circular surfaces on opposite sides thereof that are sized and shaped such that each of said surfaces is adapted to engage a respective vertebra when positioned therebetween;
   b) each of said surfaces including a portion of a radially outward extending thread for engaging a respective vertebra;
   c) said thread having a generally constant major diameter and a variable minor diameter; said thread minor diameter increasing uniformly along a length of said thread and approaching said major diameter near an anterior end of said cage so as to reduce thread depth and to provide greater support to the anterior end of vertebrae during usage.
2. The cage according to claim 1 wherein:
   a) said cage is generally cylindrical in overall shape and said surfaces each include windows passing therethrough.
3. The cage according to claim 1 wherein:
   a) said cage is a truncated cylinder with opposed semi-circular sections removed and said semi-circular surfaces are noncontinuous with each other.
4. The cage according to claim 3 wherein:
   a) said threads are noncontinuous between said semicircular surfaces.
5. The cage according to claim 1 wherein:
   a) said thread is wound in a discontinuous helical pattern about said cage.
6. The cage according to claim 1 wherein:
   a) said length over which said minor diameter increases is approximately three turns of said thread about said cage.
7. The cage according to claim 1 wherein:
   a) said minor diameter increases over approximately the anterior one fourth inch of said cage to approximately the diameter of said major diameter.
8. In a threaded fusion cage wherein a thread thereon has a minor diameter and a major diameter, the improvement comprising:
   a) said major diameter is generally constant and said thread is anteriorly feathered to progressively increase the minor diameter of said thread near an anterior end of said cage to approximate said major diameter so as to reduce thread depth.
9. The cage according to claim 8 wherein:
   a) said thread is anteriorly feathered for approximately one fourth inch.

* * * * *